United States Patent
Li et al.

(10) Patent No.: US 8,138,496 B2
(45) Date of Patent: Mar. 20, 2012

(54) ADDRESSABLE TRANSISTOR CHIP FOR CONDUCTING ASSAYS

(75) Inventors: Changming Li, Singapore (SG); Chang Qing Sun, Singapore (SG)

(73) Assignee: Nanyang Technological University, Singapore (SG)

(*) Notice: Subject to any disclaimer, the term of this patent is extended or adjusted under 35 U.S.C. 154(b) by 0 days.

(21) Appl. No.: 11/547,406

(22) PCT Filed: Apr. 1, 2005

(86) PCT No.: PCT/SG2005/000113
§ 371 (c)(1),
(2), (4) Date: Oct. 2, 2006

(87) PCT Pub. No.: WO2005/095938
PCT Pub. Date: Oct. 13, 2005

(65) Prior Publication Data
US 2008/0012007 A1    Jan. 17, 2008

Related U.S. Application Data

(60) Provisional application No. 60/558,117, filed on Apr. 1, 2004.

(51) Int. Cl.
*H01L 27/28* (2006.01)
*H01L 51/40* (2006.01)
(52) U.S. Cl. ............... 257/40; 257/253; 438/48; 438/49
(58) Field of Classification Search .............. 257/40, 257/253; 438/49, 48
See application file for complete search history.

(56) References Cited

U.S. PATENT DOCUMENTS

| | | | |
|---|---|---|---|
| 5,200,633 A * | 4/1993 | Dickert et al. | 257/253 |
| 2003/0143726 A1 * | 7/2003 | Osman et al. | 435/287.2 |
| 2003/0211502 A1 * | 11/2003 | Sauer et al. | 435/6 |
| 2004/0180463 A1 * | 9/2004 | Chou et al. | 438/49 |
| 2008/0128687 A1 * | 6/2008 | Armgarth et al. | 257/40 |

FOREIGN PATENT DOCUMENTS

| | | |
|---|---|---|
| EP | 1 085 319 A1 | 3/2001 |
| WO | WO 03/079003 A2 | 9/2003 |
| WO | WO 2004/048962 A1 | 6/2004 |
| WO | WO 2004/057027 A1 | 7/2004 |
| WO | WO 2004/106891 A2 | 12/2004 |

* cited by examiner

*Primary Examiner* — Cuong Q Nguyen
*Assistant Examiner* — Cathy N Lam
(74) *Attorney, Agent, or Firm* — Dinsmore & Shohl LLP (57) ABSTRACT

A bioelectronic microchip formed on a substrate (16) includes a plurality of field effect transistors (10), each including first (12) and second (14) electrodes on the substrate; and a channel (18) extending between the first and second electrodes. An organic semiconducting material fills the channel (18); and a dielectric layer (20) formed atop the first and second electrodes and the channel. An electrolyte (22) to hold a probe molecule may be formed on the dielectric. A third electrode (24) in proximity with the first and second electrodes and isolated therefrom contacts the dielectric. Capture of target molecules may be detected at each transistor through changes in source to drain characteristics. The method provides high density and low cost sensors, particularly in diagonistic and drug discovery applications.

19 Claims, 5 Drawing Sheets

AFTER TREATMENT

FIG. 6B

ADDRESSABLE TRANSISTOR CHIP FOR CONDUCTING ASSAYS

CROSS-REFERENCE TO RELATED APPLICATIONS

This application claims benefits from U.S. Provisional Patent Application No. 60/558,117 filed Apr. 1, 2004, the contents of which are hereby incorporated herein by reference.

FIELD OF THE INVENTION

The present invention relates generally to addressable biochips, and more particularly to chips incorporating field effect transistors and methods of use thereof. Embodiments of the invention can be used in assays to detect molecular interactions such as nucleic acid hybridization, protein binding or other chemical/electrochemical reactions.

BACKGROUND OF THE INVENTION

Chemically modified field effect transistor (CHEMFET)-based sensor technologies have been studied as they have potential as microsensors for food, biomedical and environmental analytics. CHEMFETs have advantages over conventional ion-selective electrode-based sensors in terms of small dimensions, low-output impedance, fast response, mass-fabrication ability and great potential for integration into smart sensor arrays for detecting multi-analytes. However, present devices are mainly based on inorganic metal-oxide-semiconductor field effect transistors (MOSFETs). A limiting factor of such MOSFET devices is the relatively high manufacturing costs. This is particularly true for clinical applications which have strict safety requirements and where the use of disposable microsensors is highly desirable.

Biochips, including DNA and protein array-based devices, have become an important tool in the life sciences, biomedical applications and drug discovery, due to the many benefits of miniaturization, integration and high-throughput mode of operation. Existing biochip technology is based however on fluorescent-based glass or silicon array fabrication and can be very expensive. For more than a decade now, organic field effect transistors (OFETs) based on conjugated polymers, oligomers, or other organic molecules have been envisioned as a viable alternative to more traditional, mainstream thin-film transistors (TFTS) based on inorganic materials.

A major obstacle in the development of an addressable electronic array biochip is the occurrence of ionic shortage of different sensing arrayed electrodes because of the electrolytes in the sample. US 2002009064A1 discloses a high density addressable array biochip for electronic detection, which uses microchannels to separate different column arrays to eliminate the ionic shortage problem of addressed arrayed electrodes. The microfluidic method used however results in a much higher chip production cost and it is also very difficult to fabricate nano-array chips which require the nanoscale channels for eliminating the ionic shortage.

There thus remains a need to develop more efficient devices and methods to fabricate electrical or electrochemical array chips. Particularly, there remains a need in the art to develop low cost column-and-row addressable biochip arrays for the electrical or electrochemical detection of molecular interactions that can be easily and cost-effectively fabricated and that reduces the cost of performing various analyses, while increasing the effectiveness and utility thereof. More particularly, there remains a need in the art to develop electronic addressable biochips.

SUMMARY OF THE INVENTION

In accordance with an aspect of the present invention, a bioelectronic microchip includes: a substrate; a plurality of field effect transistors, each including: a first and second electrodes on the substrate; and a channel extending between the first and second electrodes; a semiconducting material filling the channel; a dielectric layer formed atop the first and second electrodes and the channel; a third electrode in proximity with the first and second electrodes and isolated therefrom.

A solid or gel polymer electrolyte is coated atop of the dielectric layer. A potential applied to the third electrode exerts an electric field modulating the semiconducting channel of an associated transistor between the pair of electrodes through the solid/polymer electrolyte.

In an embodiment, probe molecules of a certain type may be immobilized in the solid electrolyte on top of the dielectric layer. As a result, the modulation depth of the channel will depend on the electrical properties of the probe molecules. The probe molecules may be immobilized through entrapment or covalent binding thus allowing sensing target molecules through known chemical affinity or reactions.

In an alternative embodiment, probe molecules of a certain type may be directly immobilized on the dielectric coating for sensing target molecules through chemical affinity or reactions. Again, a modulation depth of the channel depends on electrical properties of probe/target molecule combination.

In an alternative embodiment, small covalent binding linker molecules can be grafted into dielectric layer by mixing the liker material and the dielectric material before forming the dielectric layer. Probe molecules of a certain type may be immobilized on the dielectric coating by covalent binding through the embedded linkers. Again, a modulation depth of the channel depends on electrical properties of probe/target molecule combination.

The first and second electrodes act as drain/source electrodes, and the third electrode acts as a reference electrode (akin to the gate electrodes in a MOSFET).

In accordance with another aspect of the present invention, the bioelectronic microchip may be all-printed and/or coated from solutions or/and inks to form an all-printed organic chemical field effect transistor with extremely low manufacturing and material costs.

The plurality of field effect transistors may also be formed in a two dimensional array on the substrate. All first electrodes in a row are electronically interconnected (and may, for example be addressed as x1, x2). All second electrodes in a column are electronically interconnected (and may for example be addressed as y1, y2, ... ). All third electrodes may be electronically interconnected together as common line.

The multiple transistors are thus x-y addressable. In an embodiment, a x-y addressable biochip forms to significantly reduce the multiplexing I/O lines in a high density array biochips.

In accordance with another aspect of the present invention, an addressable bioarray, comprises a plurality of organic field effect transistors formed in a substrate, each of the field effect transistors including a source, and a drain; a channel formed therebetween and dielectric layer on the top of them. An electrolyte is formed atop the dielectric layer, to receive an analyte. A third electrode extends into the electrolyte. The presence of an analyte changes the channel characteristics under modulation of the third electrode, and may be detected through the source/drain electrodes. Preferably, areas of the biochip other than those covered by the electrolyte are coated with a hydrophobic material to eliminate ionic shortage. The different columns/rows of electrodes are thus isolated by hydrophobic substrate, allowing the sample solution after the probes incubation with the target molecules to be blown out or drained out, for the subsequent electronic detection at different detection array spots.

In accordance with another aspect of the present invention, there is provided a method of forming a biochip, by forming a plurality of transistors in a substrate.

Each transistor may be formed by printing, coating, vacuum deposition or otherwise forming parallel source and drain regions on a substrate separated by a gap. The gap defines a channel.

Each channel is filled with an organic semiconduction material. A dielectric layer is coated on the top of the source/drain electrodes and is coated a solid or gel polymeric electrolyte to receive an analyte. Electrodes are formed in the electrolyte regions. The transistors are arranged in an array. Regions of the biochip that are not covered with electrolyte may further be covered with a hydrophobic coating. The size of each transistor is preferably in the nano-meter order.

Additional source/drain electrodes extend from the transistors. Source/drain electrodes of transistors in rows are interconnected. The electrodes connected to the electrolytes of transistors in a column are also interconnected. This allows for row/column addressing of the organic chem./bio transistors. The channel may be filled by inkjet printing or chemical vaporation deposition method.

In an embodiment, the organic transistor may be completely formed on an insulating bulk substrate, which can, for example, be made from materials such as plastic, ceramic, glass, paper, rubber, fabric, printed circuit board, silicon or combinations thereof. Conveniently, multiple CHEMOFETS may be formed in an addressable array. The addressable array electrode material can be, for example, solid or porous gold, silver, platinum, copper, titanium, chromium, aluminum, metal oxide, metal carbide, carbon, graphite, fullerene, conductive plastic, conductive polymer, metal impregnated polymers, nanocarbon tube, organic or polymer conducting wires or combinations thereof. All components of the biochip can thus be printed, including the organic transistor composed parts (conductors, source, drain, organic semiconductor and insulation layer) and the sensing transducer parts (reference electrode, polymer gel electrolyte).

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures which illustrate by way of example only, embodiments of the present invention.

DETAILED DESCRIPTION

The invention provides a chemically modified organic field effect transistor (CHEMOFET) based and column-and-row addressable array biochip. Embodiments utilize all printed OFETS in both the sensing and detecting components, combining molecular electronics (building a detection circuit with OFET) and bioelectronics (building an electronic biochip with OFET) to allow the manufacture of a high density array.

Figure 1:
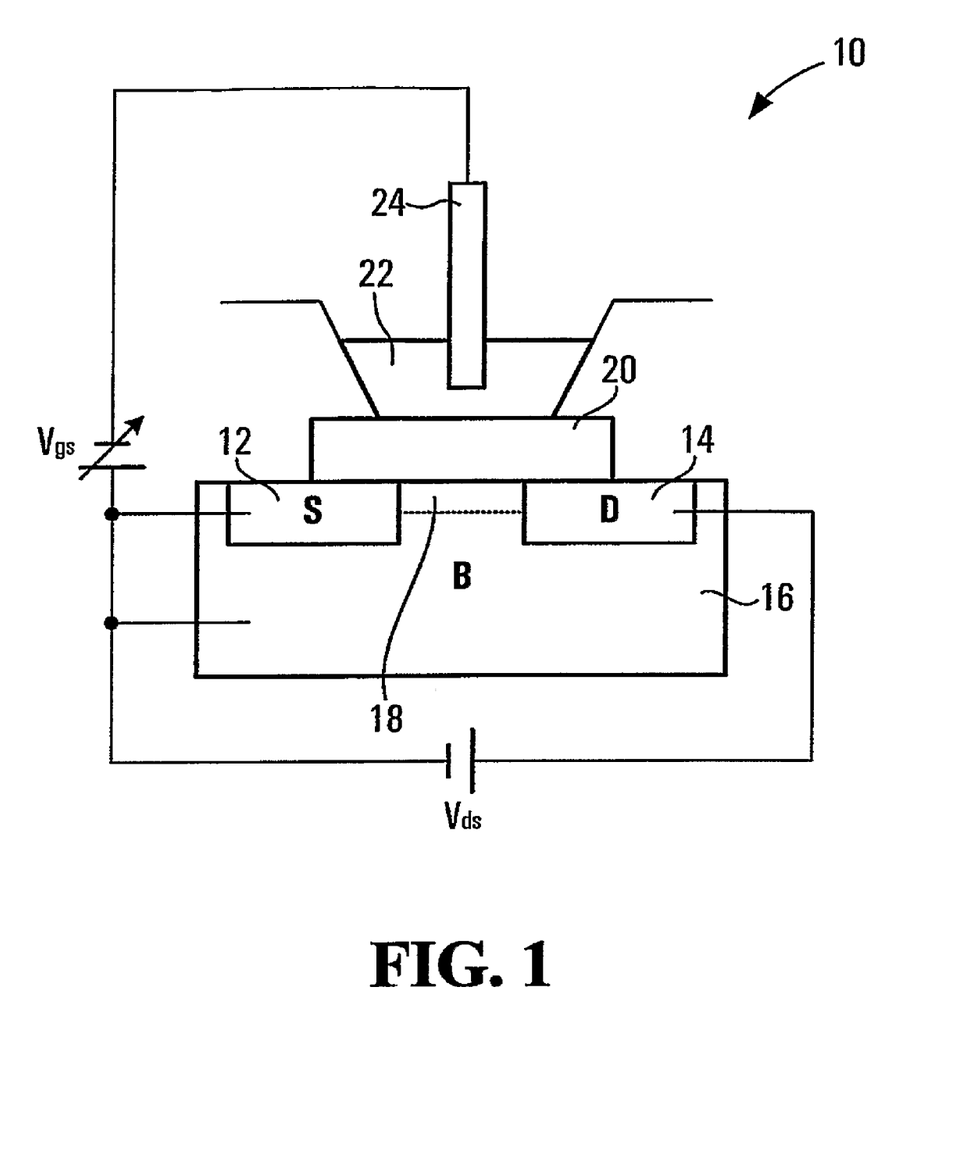
FIG. 1 is a schematic diagram of a chemically modified organic field effect transistor.

An example single OFET 10 that may be used as a sensor is illustrated in FIG. 1. As illustrated, source and drain electrodes 12, 14 are formed in a semiconducting substrate 16. A channel 18 is formed between source and drain electrodes 12, 14. A dielectric insulating layer 20 is formed atop channel 18. Layer 20 is coated with an electrolyte 22. A reference electrode 24 contacts electrolyte 22 as a substitute for a conventional gate electrode. Probe molecules (not shown) are immobilized in dielectric layer 20 or in electrolyte 22 on top of the dielectric layer 20. Probe/target molecule interaction may change the electrical properties of the dielectric layer 20 thus allowing for the sensing of target molecules in samples. Different analytes or different concentrations of the same analyte in the electrolyte can modify dielectric layer 20 of OFET 10, resulting in different changes of density of electrons in the inversion layer built by imposing voltage between the reference electrode and the source electrode. Typically, the changes very sensitively correspond to the concentration of the analyte.

Figure 2:
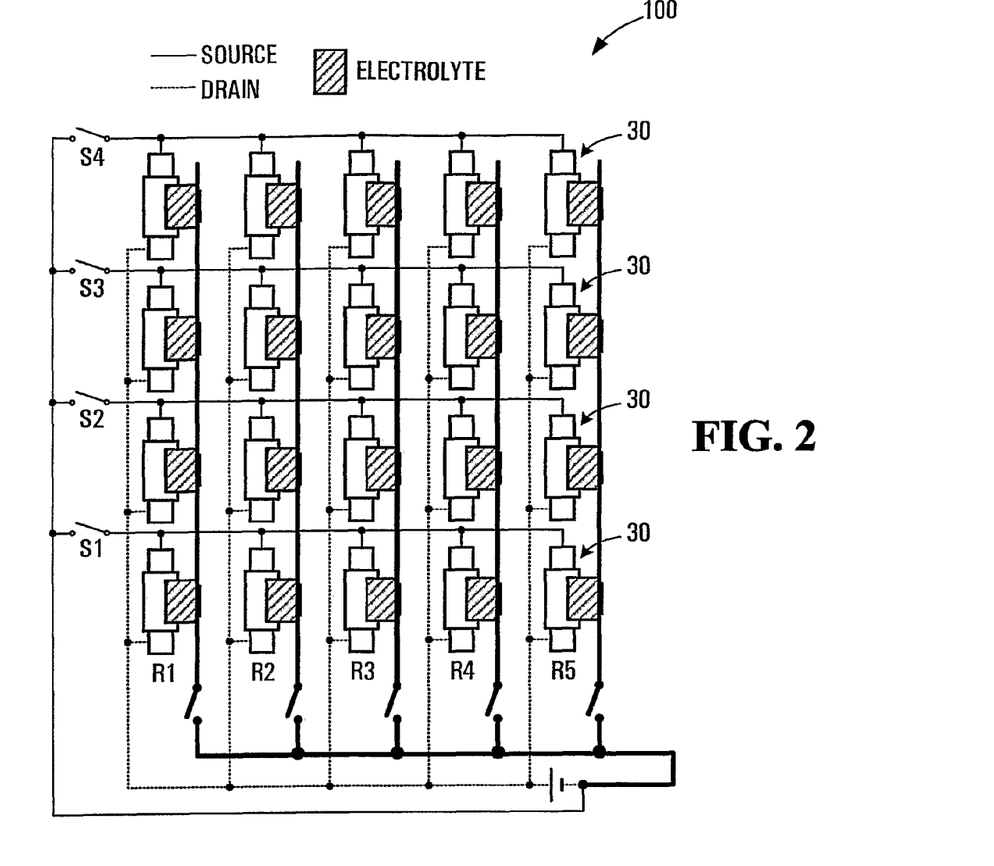
FIG. 2 is a schematic diagram of a biochip, exemplary of an embodiment of the present invention.

FIG. 2 schematically illustrates an exemplary source/reference electrode addressable OFET array biochip 100. Chip 100 includes a plurality of OFETs 30, similar to OFET 10 of FIG. 1, arranged in rows and columns on a substrate 102. As will become apparent, OFETs 30 may be printed or vapour deposed on substrate 102. For nanoscale printing, atomic force microscopy may be used as tool for the nanoprinting.

Figure 3:
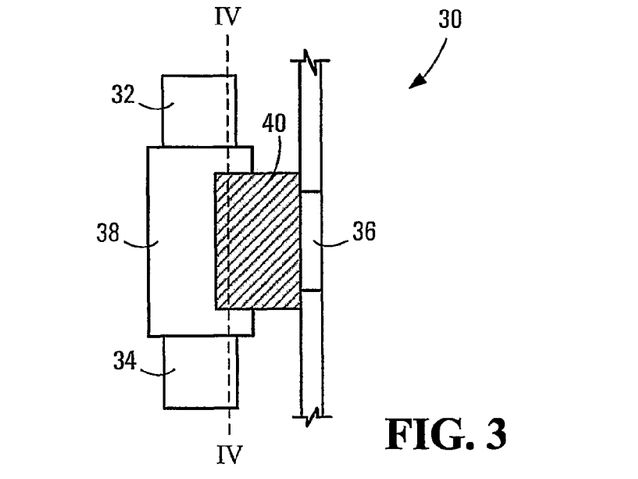
FIG. 3 is a plan view of an organic field effect transistor of the biochip of FIG. 2.
Figure 4:
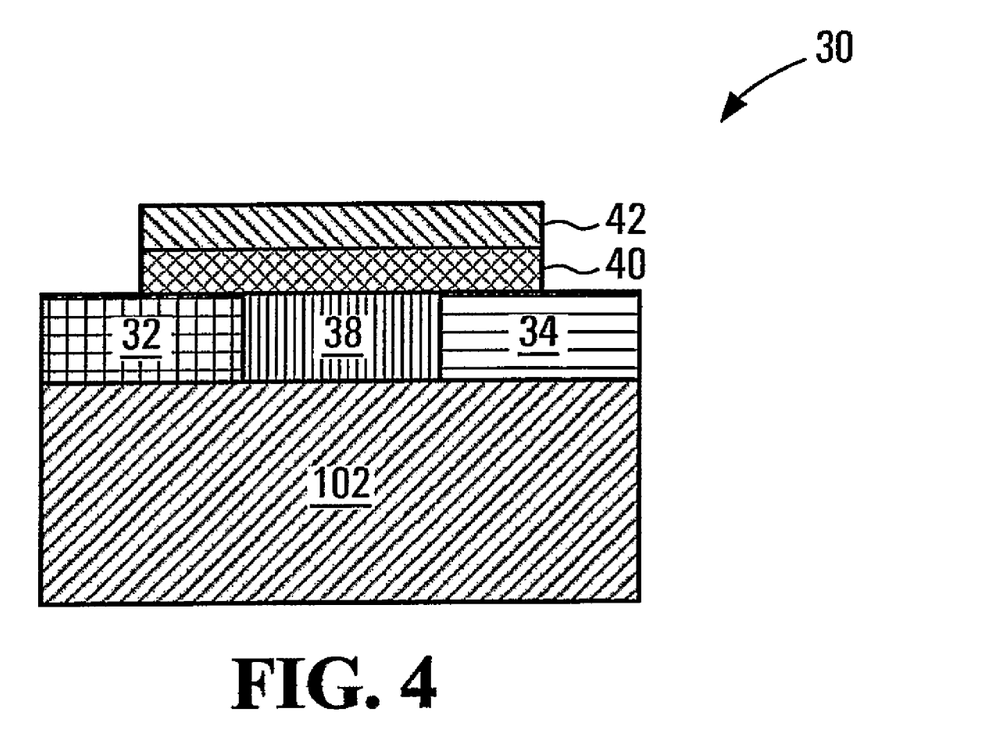
FIG. 4 is a schematic sectional view of a chemically modified organic field effect transistor of FIG. 3, along lines IV-IV.

Enlarged plan and cross-sectional schematic views of each individual OFETs 30 are illustrated in FIGS. 3 and 4. As illustrated, each OFET 30 includes source and drain electrodes 32 and 34 spaced from each other. An organic semiconducting material is formed in the space between source and drain electrodes 32, 34 to form a conductive channel 38 therebetween. The organic semiconducting material may, for example, be selected from polythiophene, polyacetylene, phthalocyanine, poly(3-alkylthiophene), α,ω-hexathiophene, pentacene, α,ω-dihexylhexathiophene, poly(thienylene vinylene), C60, bis(dithienothiophene), α,ω-dihexylquaterthiophene, dihexylanthradithiophene, fluorinated NTCDI, α,ω-dihexylquinquethiophene, or their combinations. A dielectric insulator 40 at least partially covers channel 38. An electrolyte layer 42 is formed atop insulator 40. As will be appreciated the depth of channel 38 may be controlled by the voltage applied to electrolyte 42.

A reference electrode 36 is formed next to, and in proximity with source and drain electrodes 32, 34, and is covered with electrolyte 42.

Reference electrodes 36 of all OFETs 30 within a column are interconnected. A single reference electrode thus serves all source and drain electrodes 32, 34 of OFETs 30 in the same column. Similarly, all source electrodes 32 within a row are interconnected to each other, and all drain electrodes 34 within a column are interconnected.

Electrolyte 42 may be solid or gel, and may for example be polyacrylamide. Electrolyte 42 acts as a receptacle for analyte solutions. Electrolyte 42 is pattern-coated or deposited in such a way that the electrolyte 42 of each OFETs 30 does not overlap with the electrolyte of adjacent OFETs 30. This is best illustrated in FIG. 2.

The remaining surface of biochip 100 is coated with a hydrophobic layer (not shown). The hydrophobic layer is much thinner than electrolyte 42, and therefore allows only the electrolyte 42 or dielectric layer 40 to be exposed.

In this embodiment, OFETs 30 are printed onto the insulating bulk substrate, which can, for example, be made from materials such as plastic, ceramic, glass, rubber, fabric, printed circuit board, silicon or combinations thereof. The electrode material can be, for example, solid or porous gold, silver, platinum, copper, titanium, chromium, aluminum, metal oxide, metal carbide, carbon, graphite, fullerene, conductive plastic, conductive polymer, metal impregnated polymers or combinations thereof. As will become apparent, all components of biochip 100 can be printed, including the components of OFETs 30 (conductors, source, drain, organic semiconductor and insulation layer) and reference electrode, and polymer gel electrolyte.

Figure 5:
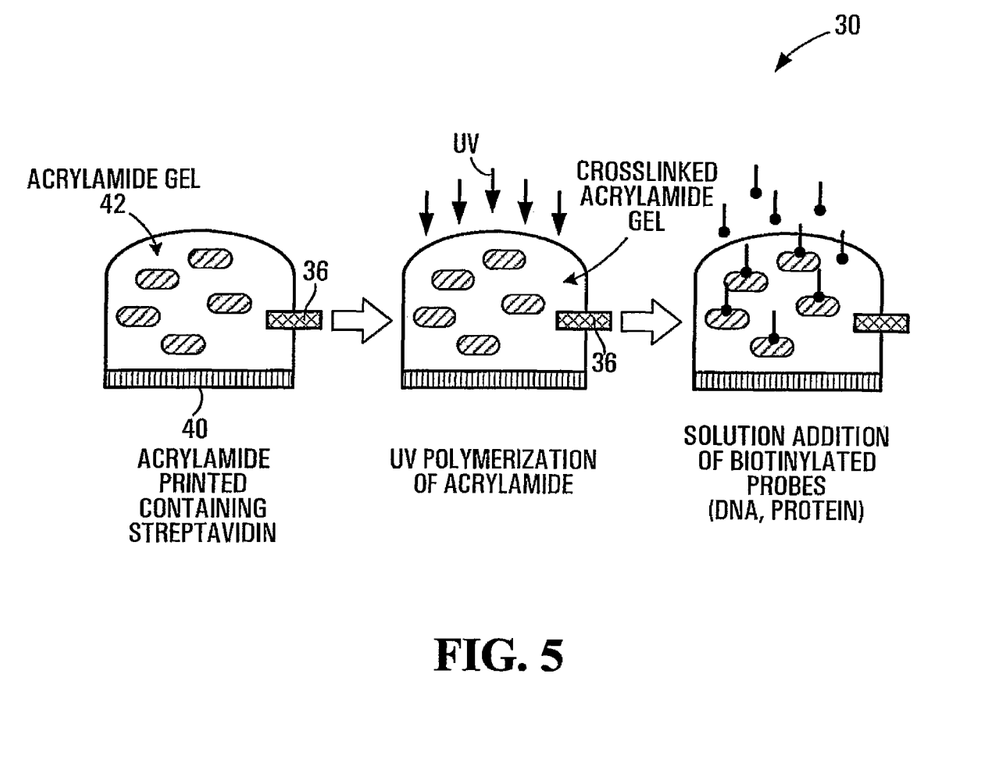
FIG. 5 is schematic process diagram illustrating formation of an exemplary electrolyte layer for use in an organic field effect transistor of the biochip of FIG. 2.

As schematically illustrated in FIG. 5, probe molecules that bind to specific target molecules, may be embedded in, or attached to, electrolyte 42. Electrolyte 42 is thus used as both an ionic conductor and sensing transducer, to interact with analyte applied to the surface of biochip 100. Electrolyte 42 can be used as the matrix for universal bioconjugation to immobilize probe molecules. In one embodiment a certain percentage of streptavidin molecules may be mixed into a polymer gel forming electrolyte 42, which for example can be polyacrylamide gel that is porous, followed by UV crosslinking, which makes the gel insoluble and which can also function as an electrolyte.

As another example, biotinylated protein or DNA probes can be directly attached to the gel electrolyte 42 by biotin-streptavidin conjugation, as shown in FIG. 5. Only the section of the gel on the insulation layer 40 that contains streptavidin, which can be made by separately printing the gel electrolyte to overlap both the insulation layer and the reference electrode, is shown.

Alternatively, cross-linked polyacrylamide can be directly immobilized with probes by reacting the amino groups of lysine with NHS esters, providing a biocompatible aqueous environment for protein interactions through gel aldehyde groups and amino groups of the probe proteins.

Biochip 100 can thus be used to detect molecular interactions such as nucleic acid hybridization, protein binding or other chemical/electrochemical reactions.

In a further embodiment, the probe molecules may be directly immobilized on dielectric insulation layer 40 before electrolyte coating. The immobilization may be conducted by adding bioconjugation linker molecules into dielectric materials. In this case, layer 42 coating is thinner and more porous for target molecule access.

Of course, each OFET 30 on a biochip 100 may include its own (and thus possibly different) pre-selected probe molecule.

In operation, target molecules in sample analyte (typically in a solution) that may interact with the probe molecules are placed on the electrolyte 42 at individual OFETs 30. Analyte, if present, may be immobilized on electrolyte 42 by complementary probe molecules. The sample solution may be drained to facilitate electronic detection of the analyte at the different detection array spots. As only the insulation layer 40, reference electrode 36 and the coated solid or gel electrolyte 42 is exposed to the sample, and all other components and surfaces (such as source/drain electrodes and conductors) are insulated with the hydrophobic coating, ionic shortage is prevented, making detection very simple. Conveniently, leakage current is reduced by the coating hydrophobic polymer layer. This, in turn, enhances modulation of current through channel 38 in the presence of analyte. Additionally, a hydrophobic surfactant may be used to reduce moisture adsorption. The hydrophobic layer covering all exposed current connectors or part of electrode surface also prevents possible gas during OFET measurement. The organic semiconductor and insulation material should also be chemically compatible to reduce interfacial resistance.

As will be appreciated, the presence of trapped analyte at an OFETs 30 will affect the conductivity of a channel 38 beneath insulation layer 40 and electrolyte 42 of that OFET 30. This change in conductivity may be detected by detecting changes source to drain conductivity for applied voltage. That is, source and drain voltages may be individually applied to each source/drain pair and resulting current flow may be measured. This can be conducted by simply multiplexing switches (not shown) to different source/reference electrode addresses, such as S1R1, S2R2 etc for detection at different array spots (where S1, S2, . . . represent source electrode addresses and R1,R2, . . . represent the reference electrode addresses as shown in FIG. 2). Use of addressable array chips significantly reduces the number of I/O lines for much simpler multiplexing, thus further reducing the manufacturing cost of the detection system.

Advantageously, embodiments of the present invention utilise an addressable platform. As well, embodiments of the present invention do not require the fabrication of microchannels to prevent ionic shortage as this is prevented by the hydrophobic coating.

Conveniently, biochip 100 can be manufactured at a low cost. All-printed OFETs may be formed using a conventional bottom-up fabrication process with inexpensive materials. Initially, source drain and reference electrodes 32, 34 and 36 may be printed or vapour deposited, or laser cutting in metal coated isolated substrate. Organic semiconductor material may be printed or vapour deposed between source and drain electrodes. Thereafter, insulating regions 40, electrolyte 42 and hydrophobic layer may be formed on the printed electrodes and gates. Exemplary embodiments may be formed as micro- and nano-scale biochips, as the organic inks can be tailored for nano-printing with imprinting, AFM assist and/or self-assembly process. Each OFET 30 may thus be formed, for example, with dimensions less than 200 µm×200 µm and typically between 10 nm×10 nm to 200 µm×200 µm. This allows miniaturisation to make portable electronic detection devices. The nano-scale OFETs can thus be used to build array sensors or wireless networking bio/chemical sensors.

Embodiments of the present invention further provide a biochip with a universal bioconjugation method for the immobilization of multi-biomolecular probes, which has so far not been used for field effect transistors or OFETs.

As illustrated, exemplary embodiments provide an electronic detection method for biochips that is based on the modulation of the field effect transistor, which is a label-less method. The label-less method is important in protein array chips where the proteins are very difficult to label, for example low molecular weight protein molecules without an additional epitope for biomolecular labelling.

Electrical or electrochemical detection of molecular interactions, as used in biochip 100 also require less expensive detection systems and less instrumentation than detection techniques relying on radioactive or fluorescent labels that require photonic sensors.

Optionally biochip 100 may be plasma treated to reduce leakage current at OFETs 30. For example a biochip 100 once formed may be subjected to plasma surface treatment as follows:

1. The surface of the substrate may be cleaned, using for example, flowing nitrogen gas.
2. The substrate may be dried (e.g. in a vacuum at 120 C for 1 hour).
3. Plasma Enhanced Chemical Vapour Deposition (PECVD) may be used to treat the biochip (e.g. under Ar 150 W for 1 min in a PECVD system).
4. The biochip may be plasma treated—by, for example, applying $NH_3$ plasma at 150 W for 10 mins by placing the biochip in a $NH_3$ purged plasma chamber.
5. Cast the P3HT-Toluene solution onto the substrate to cover the gap between source and drain.
6. Then placed the biochip with P3H-T in an oven to dry and anneal the biochip at 70 C for 1 hr.

Figure 6A:
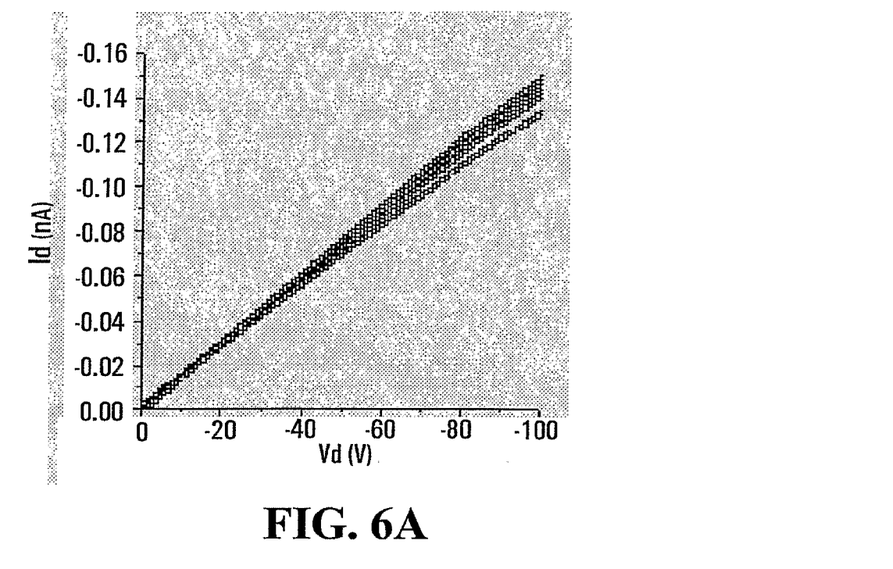
FIGS. 6A and 6B are I-V curves illustrating an example biochip in use.
Figure 6B:
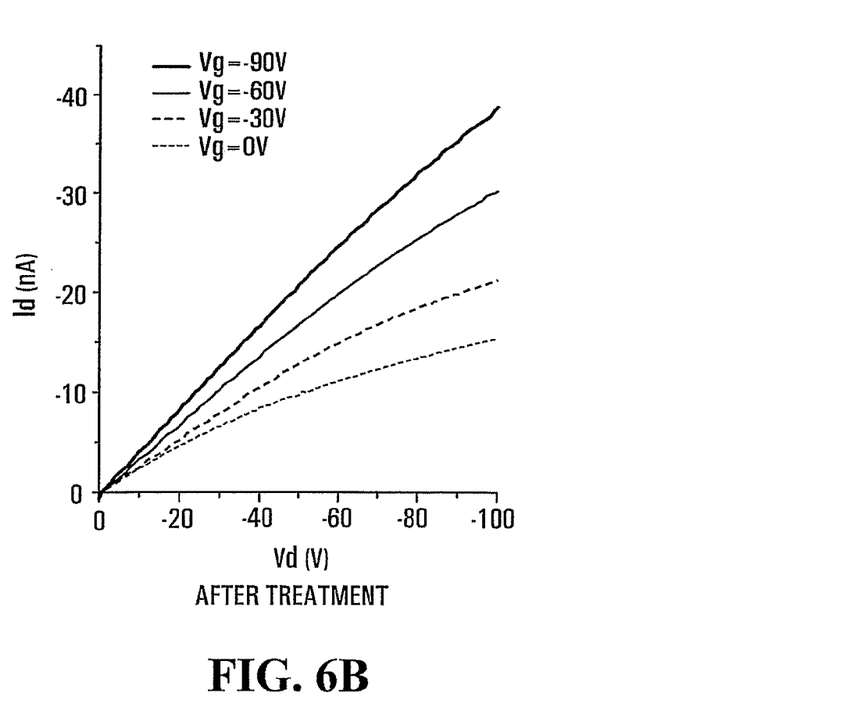

I-V curves at individual OFETs were measured with and without plasma treatment, as shown in FIGS. 6A and 6B. Before treatment with plasma, the organic transistor had poorer modulation shown in FIG. 6A. After plasma-treatment, the transistor performance was improved. Measurement also demonstrated the leakage current of OFETs was much reduced in comparison to the biochip without plasma treatment. The Plasma treatment could remove some conductive impurity on the surface components of the biochip, this could give better modulation and reduce the leakage current.

As should now be appreciated, biochip 100 has various applications, for example in clinical diagnostics, drug discovery, food safety, and environmental protection.

Of course, the above described embodiments are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

What is claimed is:

1. A chip for detecting the presence of at least one analyte, comprising:
    a substrate;
    a plurality of organic field effect transistors, arranged in a two dimensional array on said substrate, each of said organic field effect transistors including:
        a first and second electrodes printed on the substrate; and a channel extending between the first and second electrodes;
        an organic semiconducting material filling the channel;
        a dielectric layer formed atop the first and second electrodes and the channel;
        a third electrode in proximity with the first and second electrodes and isolated therefrom, wherein each of said field effect transistors further comprises an exposed electrolyte coated atop of its dielectric layer and in contact with its third electrode, said dielectric layer electrically insulating said channel from said exposed electrolyte, said exposed electrolyte, exposed to receive an analyte, whereby the presence of the analyte when received on the exposed electrolyte atop of the dielectric layer of the field effect transistor influences electrical characteristics of the channel under modulation of the third electrode, and may be detected through the first and second electrodes, and
        a hydrophobic coating covering the remaining surface of said substrate not covered by said electrolyte.

2. The chip of claim 1, wherein, probe molecules of a certain type are immobilized in the exposed electrolyte of each of said field effect transistors.

3. The chip of claim 1, wherein probe molecules of a certain type are immobilized on the dielectric layer of each of said field effect transistors for sensing target molecules through chemical affinity or reactions.

4. The chip of claim 3, wherein said probe molecules of a certain type are immobilized on the dielectric layer of each of said field effect transistors by pre-embedded linker molecules.

5. The chip of claim 1, wherein each of said first and second electrodes, said dielectric and said semi-conducting material are printed on said substrate.

6. The chip of claim 1, wherein said field effect transistors are arranged in a two dimensional array on said substrate.

7. The chip of claim 6, wherein said first electrodes in each row of said two dimensional array are electronically interconnected.

8. The chip of claim 7, wherein said third electrodes in each column of said two dimensional array are electronically interconnected.

9. The chip of claim 1, wherein said second electrodes of all of said field effect transistors are electronically interconnected.

10. A device for performing assays, comprising an addressable plurality of organic field effect transistors formed on an insulating substrate, each of said field effect transistors including
    a source;
    a drain;
    a channel formed of an organic semiconducting material, extending between said source and drain,
    wherein said source, drain and channel are printed on said insulating substrate;
    a dielectric layer on top of said channel;
    an exposed electrolyte formed atop said dielectric layer and exposed to receive an analyte, and
    extending onto an electrode; and
    a hydrophobic coating covering the remaining surface of said substrate not covered by said exposed electrolyte,
    whereby the presence of an analyte influences electrical characteristics of said channel under modulation of the electrode, and may be detected through the source and drain;
and wherein said plurality of field effect transistors are interconnected to each other to be individually addressable to detect the presence of analyte on particular ones of said plurality of transistors.

11. The device of claim 10, wherein the exposed electrolyte of different ones of said transistors have differing probe molecules embedded or attached thereto.

12. The device of claim 10, wherein the exposed electrolyte is formed of polymeric gel.

13. The device of claim 10, wherein each of said transistors occupies less than 200 $\mu m \times 200$ $\mu m$.

14. The chip of claim 1, wherein the exposed electrolyte of different ones of said transistors have differing probe molecules embedded or attached thereto.

15. The chip of claim 1, wherein the exposed electrolyte of each of said transistors is formed of polymeric gel.

16. The chip of claim 1, wherein each of said transistors occupies less than 200 μm×200 μm.

17. The chip of claim 1, wherein said exposed electrolyte comprises streptavidin.

18. The device of claim 10, wherein said plurality of transistor are arranged in rows and columns, and wherein the electrode of each of said transistors in a column are electrically interconnected.

19. The device of claim 18, wherein the source of each of said transistors in a row are electrically interconnected.

* * * * *